United States Patent [19]
Corio et al.

[11] Patent Number: 5,998,212
[45] Date of Patent: Dec. 7, 1999

[54] METHOD FOR FLEXIBLY SORTING PARTICLES

[75] Inventors: Mark A. Corio; James F. Leary, both of Rochester, N.Y.

[73] Assignee: University of Texas Medical Branch at Galveston, Galveston, Tex.

[21] Appl. No.: 08/697,296

[22] Filed: Aug. 26, 1996

Related U.S. Application Data

[62] Division of application No. 07/990,718, Dec. 15, 1992, Pat. No. 5,550,058, which is a division of application No. 07/681,559, Apr. 5, 1991, Pat. No. 5,199,576.

[51] Int. Cl.⁶ .............................. B07C 5/04; B07C 5/342; G01N 15/00
[52] U.S. Cl. ........................ 436/63; 422/68.1; 209/3.1; 209/579; 209/906
[58] Field of Search .................................. 436/8, 63, 800; 209/906, 579, 3.1; 422/82.01, 68.1

[56] References Cited

U.S. PATENT DOCUMENTS

| | | | |
|---|---|---|---|
| 3,675,768 | 7/1972 | Legorreta-Sanchez | 209/906 |
| 3,710,933 | 1/1973 | Fulwyler et al. | 209/579 |
| 3,791,517 | 2/1974 | Friedman | 209/906 |
| 3,826,364 | 7/1974 | Bonner et al. | 209/579 |
| 3,963,606 | 6/1976 | Hogg . | |
| 3,984,307 | 10/1976 | Kamentsky et al. | 209/906 |
| 4,063,284 | 12/1977 | Tatami . | |
| 4,230,558 | 10/1980 | Fulwyer | 209/579 |
| 4,317,520 | 3/1982 | Lombardo et al. | 209/906 |
| 4,318,480 | 3/1982 | Lombardo et al. | 209/906 |

(List continued on next page.)

FOREIGN PATENT DOCUMENTS

| | | | |
|---|---|---|---|
| 0025296 | 3/1981 | European Pat. Off. | G01N 15/07 |
| 0343380 | 11/1989 | European Pat. Off. | G01N 33/50 |
| 3822310 | 9/1989 | Germany . | |
| 1527462 | 10/1978 | Japan . | |
| 9010858 | 9/1990 | WIPO . | |

OTHER PUBLICATIONS

Patent Abstracts of Japan, vol. 11, No. 334 (p. 631), Oct. 31, 1987, English–language Abstract of Japanese Publication No. 62–116260.

Patent Abstracts of Japan, English–language Abstract of Japanese Publication NO. 56058676, May 21, 1981.

Peters, et al. "The LLNL High–Speed Sorter: design features operational characteristics of biological utility", vol. 6, 1985, (pp. 290–301).

Bonner, et al. "Fluorescence Activated Cell Sorting" Review of Scientific Instruments, vol. 43, No. 3, Mar. 1992, New York (pp. 404–409).

Steinkamp, "Flow Cytometry", Review of Scientific Instruments vol. 55, No. 9, Sep. 1984, New York, (pp. 1375–1400).

Wo–A–92 16829 (University of Rochester).

*Primary Examiner*—Harold Y. Pyon
*Attorney, Agent, or Firm*—Cooper & Dunham LLP

[57] ABSTRACT

This invention relates to a method and apparatus for flexibly controlling sorting decisions for a flow cytometer or similar instrument at a purity vs. yield ratio of sorted particles, particularly at high event rates. The system monitors distances between sequential objects to determine if they are in close enough proximity to be within a single resolution unit of the sorting device. The "friend" or "foe" status of neighboring events is considered by this system in dealing with detected "coincident" events. The system operates on information of the desirability to sort the object, i.e. droplet, based upon the properties of the individual object. A storage and retrieval method is provided for making the information available at the time a sort operation based on a sorting logic condition is performed. Accordingly, an easily reconfigurable mode of operation control is provided to allow customized sorting strategies, based on the needs of individual applications or experiments. This system may be included as an integral part of a flow cytometer/cell sorter or similar instrument and may also be provided as an outboard module to such systems.

6 Claims, 10 Drawing Sheets

U.S. PATENT DOCUMENTS

| | | | |
|---|---|---|---|
| 4,318,481 | 3/1982 | Lombardo et al. | 209/906 |
| 4,318,482 | 3/1982 | Barry et al. | 209/906 |
| 4,318,483 | 3/1982 | Lombardo et al. | 209/3.1 |
| 4,325,483 | 4/1982 | Lombardo et al. | 209/3.1 |
| 4,487,320 | 12/1984 | Aver | 209/3.1 |
| 4,515,274 | 5/1985 | Hollinger et al. | 209/3.1 |
| 4,526,276 | 7/1985 | Shoor et al. | 209/552 |
| 4,564,598 | 1/1986 | Briggs | 436/5.1 |
| 4,661,913 | 4/1987 | Wu et al. | 364/500 |
| 4,667,830 | 5/1987 | Nozaki et al. | 209/3.1 |
| 4,691,829 | 9/1987 | Aver | 209/3.1 |
| 4,727,020 | 2/1988 | Recktenwald et al. | 435/6 |
| 4,756,427 | 7/1988 | Gohde et al. | 209/3.1 |
| 4,770,992 | 9/1988 | Vanden Engh et al. | 435/6 |
| 4,778,593 | 10/1988 | Yamashita et al. | 209/579 |
| 4,866,283 | 9/1989 | Hill | 209/579 |
| 4,867,908 | 9/1989 | Recktenwald et al. | 436/8 X |
| 4,882,284 | 11/1989 | Kivchanski et al. | 436/63 |
| 4,957,363 | 9/1990 | Takeda et al. | 356/73 |
| 4,981,580 | 1/1991 | Auer | 209/3.1 |
| 4,986,657 | 1/1991 | Ohe | 356/73 |
| 4,987,539 | 1/1991 | Moore et al. | 364/413.08 |
| 5,030,002 | 7/1991 | North | 356/73 |
| 5,101,978 | 4/1992 | Marcus | 209/3.1 |
| 5,156,810 | 10/1992 | Ribi | 422/82.01 |
| 5,550,058 | 8/1996 | Corio et al. | 436/63 |

METHOD FOR FLEXIBLY SORTING PARTICLES

This application is a division of application Ser. No. 07/990,718, filed Dec. 15, 1992 and now U.S. Pat. No. 5,550,058 issued on Aug. 27, 1996 which is a division of application Ser. No. 07/681,559, filed Apr. 5, 1991 and now U.S. Pat. No. 5,199,576, issued on Apr. 6, 1993.

The invention was made with government support under grant number 5 R01-GM38645 from the National Institute of General Medical Sciences.

BACKGROUND AND SUMMARY OF THE INVENTION

This invention relates to a system for investigating particles, and in particular to such a system wherein sorted particles are selected at a yield/purity ratio at very high signal processing rates.

Systems for sorting minute particles in a fluid may be referred to as flow cytometer sorting systems. These systems are used in the medical research and diagnostic fields for the rapid analysis and processing of biological cells. Systems for sorting particles suspended in a liquid according to certain characteristics are discussed in U.S. Pat. Nos. 3,393,606, 4,063,284 and 4,487,320. Specifically, in these prior art systems optical measurements of characteristics of each particle of a group of particles are made while the particles are suspended in a liquid. In one such system, a flow cytometer cell sorter analyzes cells or particles in suspension which are labeled with a fluorescent marker and are carried single file in a fast-moving liquid stream sequentially through a tightly focused laser beam whose wavelength is adjusted to illuminate the fluorescent dye (Bonner, W. A., Hulett, H. R., Sweet, R. G., and Herzenberg, L. A., Fluorescence Activated Cell Sorting, Rev. Sci. Instrum. 43:3 404, 1972). The fluorescence produced during the laser beam crossing is collected by an,optical system and projected through spectral filters onto photodetectors. These detectors convert the fluorescence to electrical pulses whose amplitudes depend on the total light reaching the detectors. Particles having predetermined characteristics are recognized by their distinctive fluorescence. After measurements of the characteristics, each particle flows in a liquid jet stream until the particle reaches a point where the jet breaks into discrete droplets. At this point, an electric charge is induced on each droplet containing a particle to be sorted and the charged and uncharged droplets are then sorted electrostatically into appropriate recovery vessels.

Previously proposed methods of separating particles have also included separation on the basis of electronically measured cell volume by charging cells according to a sensed volume and detecting the charged cells in an electrostatic field for separation into collection vessels. (Fulwyler, M. J., Electronic Separation of Biological Cells by Volume, Science 150: 910, 1965). A system has also been proposed for quantitative analysis and sorting of particles based on multiple parameters to increase the ability to differentiate among cell types by measuring the differences between multiple parameters of the cells (Steinkamp, et al., A New Multiparameter Separator for Microscopic Particles and Biological Cells, Rev. Sci. Instrum., Vol. 44, No. 9, 1301 (1973). In this system, cells stained with fluorescent dyes in liquid suspension enter a flow chamber where electrical and optical sensors measure cell volume, single and two color fluorescence and light scatter to produce electrical signals. A processing signal unit processes the electrical signals according to preselected parameters and electrically charges droplets containing the desired cells. The typical rate at which cells are sorted in this system is a few hundred cells/sec.

A number of proposals have been described for multiple parameters, increasing processing speeds and accuracy of flow cytometer cell sorters. For example, systems have been proposed for electronics modularization to process as many as eight input parameters for sorting cells (Hiebert, R. D., Jett, J. H., and Salzman, G. C., Modular Electronics for Flow Cytometry and Sorting: the Lacel System, Cytometry, 1:337, 1980); a system operating at rates of 15,000–25,000 cells/sec by increasing the pressure in the jet stream to increase droplet production frequency (Peters, D., Branscomb, E., Dean, P., Merrill, R., Pinkel, D., Van Dilla M., and Gray, J. W., The LLNL.High-Speed Sorter: Design Features, Operational Characteristics, and Biological Utility. Cytometry 6:290, 1985; Peters, D., Dean, P., and Merrill, J. T., Multi-Parameter, Computer Controlled Operation of a FACS II Cell Sorter, Cytometry 2:350, 1982). Examples of systems for increasing accuracy are: a system to assure proper timing (Martin, J. C., McLaughlin, S. R., and Hiebert, R. D., A Real Time Delay Monitor for Flow-System Cell Sorters, J. Histochem. and Cytochem., 27(1): 277, 1979), sort timing a system for increasing droplet breakoff stability (Stovel, R. T., The Influence of Particles on Jet Breakoff, J. Histochem. and Cytochem. 25(7): 813, 1977; Auer, R. E., Method and Apparatus for Detecting Change in the Breakoff Point in a Droplet Generation System (analysis of blood cells), U.S. Pat. No. 4,487,320, 1984; Auer, R. E., Method and Apparatus for Detecting Change in the Breakoff Point in a Droplet Generation System (radiation sensing means), U.S. Pat. No. 4,691,829, 1987); a system describing individual cell sorting (Stovel, R. T., Individual Cell Sorting, J. Histochem. and Cytochem. 27(1): 284, 1979); a system correlating multiparameter data for each cell (Parson, J. D., Hiebert, R. D., and Martin, J. C., Active Analog Pipeline Delays for High Signal Rates in Multistation Flow Cytometers, Cytometry 64:388, 1985); and a system for parallel processing a signal from a large number of detectors (van den Engh, G., and Stokdijk, W., Parallel Processing Data Acquisition System for Multilaser Flow Cytometry and Cell Sorting, Cytometry 10: 282, 1989). Further, systems for improving the processing of electronics of flow cytometry applications with computers have been proposed (Steinkamp, J. A., Fulwyler, M. J., Coutler, J. R., Hiebert, R. D., Horney, J. L., and Mullaney, P. F., A New Multiparameter Separator for Microscopic Particles and Biological Cells, Rev. Sci. Instrum. 44: 1301, 1973; Steinkamp, J. A., and Hiebert, R. D., Signal Processing Electronics for Multiple Electronic and Optical Measurements on Cells, Cytometry 2(4): 232, 1982), and computer systems for automating cells systems with multiple samples based on multiple parameters (Arndt-Jovin, D., and Jovin, T. M., Computer-Controlled Multiparameter Analysis and Sorting of Cells and Particles, J. Histochem. Cytochem. 22: 622, 1974; Arndt-Jovin, D., and Jovin, T. M., Automated Cell Sorting With Flow Systems, Ann. Rev. Biophys. Bioeng. 7: 527, 1978). The above described proposals having the advantage of more accurately sorting cells have not allowed for flexibly determining sorting decisions based on the particular experiment performed.

In the experiments performed when objects (e.g. cells) are separated, i.e. sorted by a flow cytometer/cell sorter, at relatively slow event rates the individual objects are usually spaced a distance from each other which is sufficient to allow the objects to be separated individually. However, when the objects are sorted at higher rates, objects may be closer together and multiple objects may be present within a single sorting unit, i.e "droplet". This condition of having multiple objects within a single sorting unit is considered to be an "overlap" or "coincident" condition. Further, when objects are coincident, some fraction of the sorted objects are undesired resulting in a "contamination" of the sample.

The yield of the system is described as the number of events which are sorted by the system. Purity of the sample is described as the percentage of the sample which does not contain undesired objects sorted due to coincidence with desired objects. When a coincident condition occurs, if all the objects which are coincident are of the same type ("friends"), i.e. all the objects will be sorted into the same recovery vessel, then no losses of yield or purity will be observed. If, however, the objects which are coincident are of different types ("foes") the objects which are sorted will have a loss of purity unless the coincident objects are sorted from the desired objects. In the previously described systems, the additional sorting of coincident objects from objects of interest would lead to a loss of yield.

In the previously proposed systems which make a determination of a coincident condition, the systems take one of two approaches in determining the sorting of coincident events: either the systems do not sort any particles which are determined to be coincident or the systems ignore the coincident condition and sort all particles whether or not the particles are coincident (Steinkamp, J. A., and Hiebert, R. D., Signal Processing Electronics for Multiple Electronic and Optical Measurements on Cells, Cytometry 2(4): 232, 1982). There is no consideration taken as to whether particles are "friends" or "foes". The first approach results in a sample having all contamination removed from the sample. In this approach a condition of "maximum purity" is achieved and all sorting units with contaminating particles are discarded. In this case, the contaminating particles may be either "friends" or "foes". If they are "friends" and discarded, an unnecessary loss of yield is realized. The second approach results in a sample having a contamination of the sample with particles which are undesired, and therefore, results in a sample having less than "maximum purity". The second approach may be used in experiments in which the purpose of the experiment is to recover as many particular objects as possible (i.e. "maximum yield"). Moreover, in this type of experiment contamination is not important to the user and any sorting unit containing desired objects is recovered whether or not the sorting unit also contains a contamination.

A proposal has been made for sorting decisions with droplet charging control electronic circuitry to handle independent input signals for sorting cells in sort directions based on a sorting decision scheme employing a variety of coincidence and anticoincidence requirements (McCutcheon, M. J., and Miller, R. G., Flexible Sorting Decision and Droplet Charging Control Electronic Circuitry for Flow Cytometer-Cell Sorters, Cytometry 2: 219, 1982). In this system, a Read Only Memory (ROM) stores 16 separate sorting programs for making sorting decisions based on multiple parameters. The sorting decisions are inputted to circuits which exclude invalid sorting coincidences for cells which are detected separately yet close together in time as to result in conflicting sorting requirements. The system provides for three levels of control over sorting conflicts: 1) treat as unimportant the presence of contamination from other sorting fractions in a given sorting fraction; 2) recognize that a particular class of cells is undesirable and have the system lock out valid sorting events occurring after the undesirable cell; and 3) prevent contamination of the sorted cell by events still being processed. In that system, all events which are considered coincident are either aborted or ignored with no regard to their "friend" or "foe" status. Therefore, the system only allows sorting at either maximum purity or maximum yield.

This invention makes use of a recognition that it is desirable for particular experiments to have a contamination level which is settable by the user. Therefore, the present system sorts particles at a selected yield/purity ratio which ratio can include an intermediate value of the maximum yield and maximum purity. Moreover, the present invention flexibly sorts particles based on the needs of each individual experiment or assay, unlike prior art systems which fix sorting of particles based on either maximum purity or maximum yield. Therefore, a particular experiment which might be able to tolerate a contamination rate, for example 10% contamination, would be able to achieve a higher yield of sorted particles than if the same experiment was forced to use a system based on maximum purity. Also, unlike prior art systems, the present invention takes into consideration "friend" or "foe" status of neighboring events when determining coincidence for a more precise control of purity/yield considerations.

An additional advantage of the present system over prior art systems is that the quality of experiments at both high and low speeds can be improved. The quality of experiments at any speed can be affected by the random arrival nature of events within a sorting unit in some systems (e.g. flow cytometer/cell sorter). The sorting unit, whether defined by droplet, fluidic switching, zapping or other technology, can be considered to be a queuing length. Moreover, the arrival statistics of particles to this queue can be random or non-random. Random arrival can be described by queuing theory using poisson distribution functions. Other mathematical models may describe non-random arrival statistics of particles to the queue. Predictions of particle arrival and servicing (e.g serial or parallel processing) in queues, including multiple path and/or multiple queues can also be described. This invention makes use of the arrival statistics and servicing requirements in the queue to separate particles on the basis of yield or purity or any desired combination or ratio of these quantities.

In an exemplary and nonlimiting embodiment of the invention, a system trigger accepts incoming analog input signals, for example from commercially available particle detectors. The input signals are produced by the particle detector for all cells which pass through the system. The input signals may be generated when the surface of a cell passes by a selected point of the particle detector, i.e light scatter in a flow cytometer/cell sorter. In operation of the system, an input signal above a user determined threshold value triggers the initiation of the system and synchronizes parts of the system such as the event timer, inter-event timer and traditional data acquisition sort system.

In this embodiment of the system, an event timer is provided to measure the event time from when an input signal triggers the system to the time at which a sort pulse should be applied to a particle, i.e. a charge pulse should be applied near droplet breakoff of a flow cytometer for droplet sorting. The event time is a relative constant value that is defined by the physical separation of the signal excitation source from the location at which the sorting will occur and the velocity at which the object is traveling between these points. The event timer provides a signal to the system at the time a sort pulse should be applied to a particle.

This implementation includes an inter-event timer responsive to successive trigger signals to measure the time between system triggers. The time between system triggers is used to measure the distance between the cells and to determine if the distance is less than a user determined selected interval. If the distance is less than the selected interval, the measured cells are considered to be overlapping or coincident. The system stores the inter-event timer measurements in a buffer for use with sorting logic circuitry in making a sort decision.

In this embodiment, the sorting logic circuitry is responsive to the trigger signal, the inter-event timer measurements and respective detection signals which correspond to selected parameters of the particles to be sorted. The sorting logic circuitry operates on a user-selectable function of the inter-event timer measurements and the respective detection signals, hereafter called the sort decision logic condition. The sort decision logic condition can be selected by the user to correspond to a yield/purity ratio. In response to the sort decision logic condition, meaning that the object was of interest, a sort pulse is generated. After receiving an event timer signal, the sort pulse is applied to the object of interest and the object is sorted to an appropriate container.

DETAILED DESCRIPTION

Figure 1:
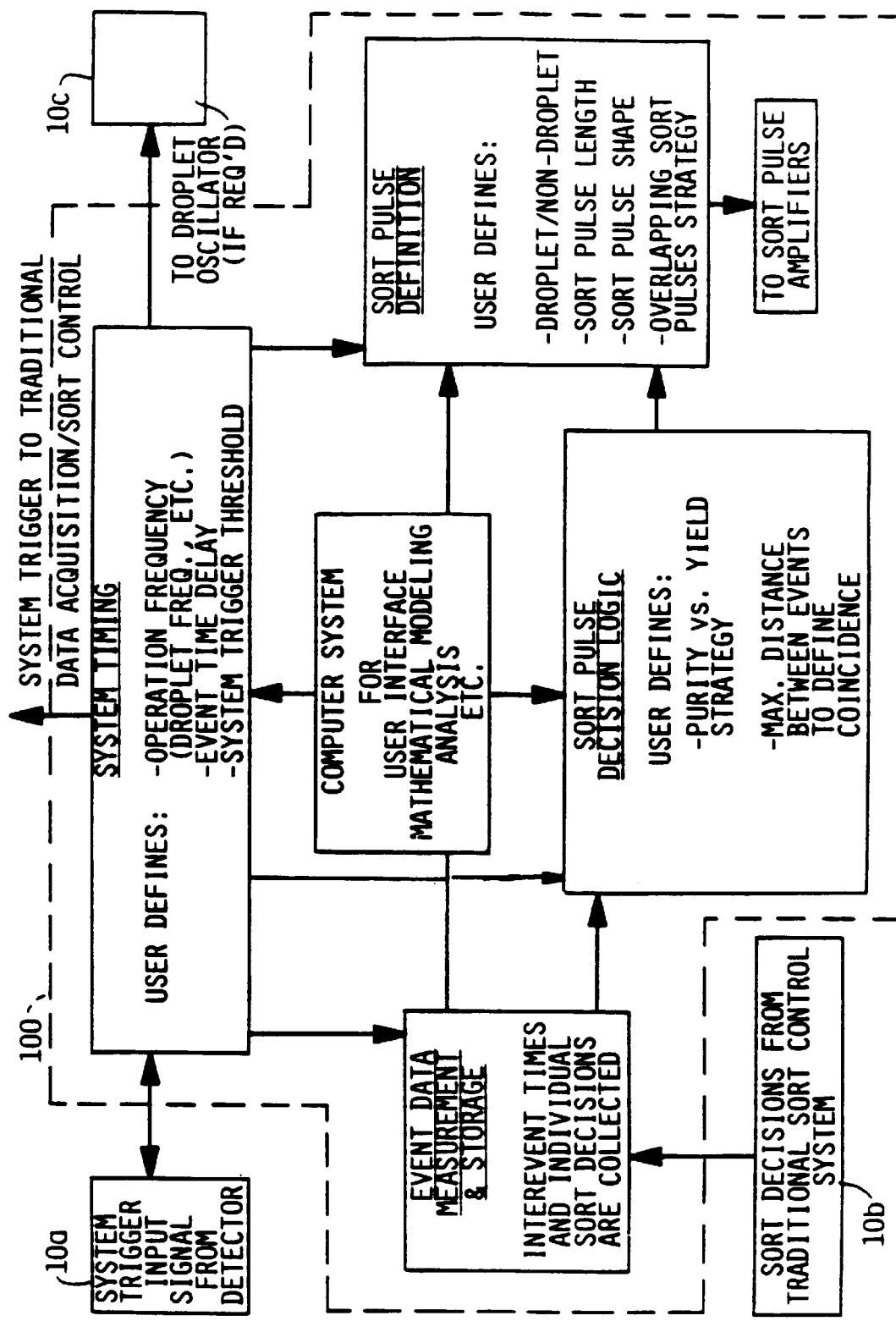
FIG. 1 is a block diagram of an embodiment of the invention system for sorting particles showing the interaction of four major functions of the system and the computer system.

FIG. 1 illustrates a block diagram of a system 100 for flexibly sorting particles in accordance with the present invention, used with a prior art flow cytometer cell sorter 10. The four major functions of this sorting system are system timing, event data measurement and storage, sort pulse decision logic, and sort pulse definition. A computer system is also provided for supplying user interface functions to the functions of the system. The computer system can also be used for mathematical modeling of the separation system to assist in defining an appropriate strategy and/or analysis of the performance of the separation system. System 100 receives input signals from photo-detectors 10a and sort decisions from traditional sort control system 10b and processes a sorting logic decision based on a logic condition, i.e. a yield/purity ratio.

Figure 2:
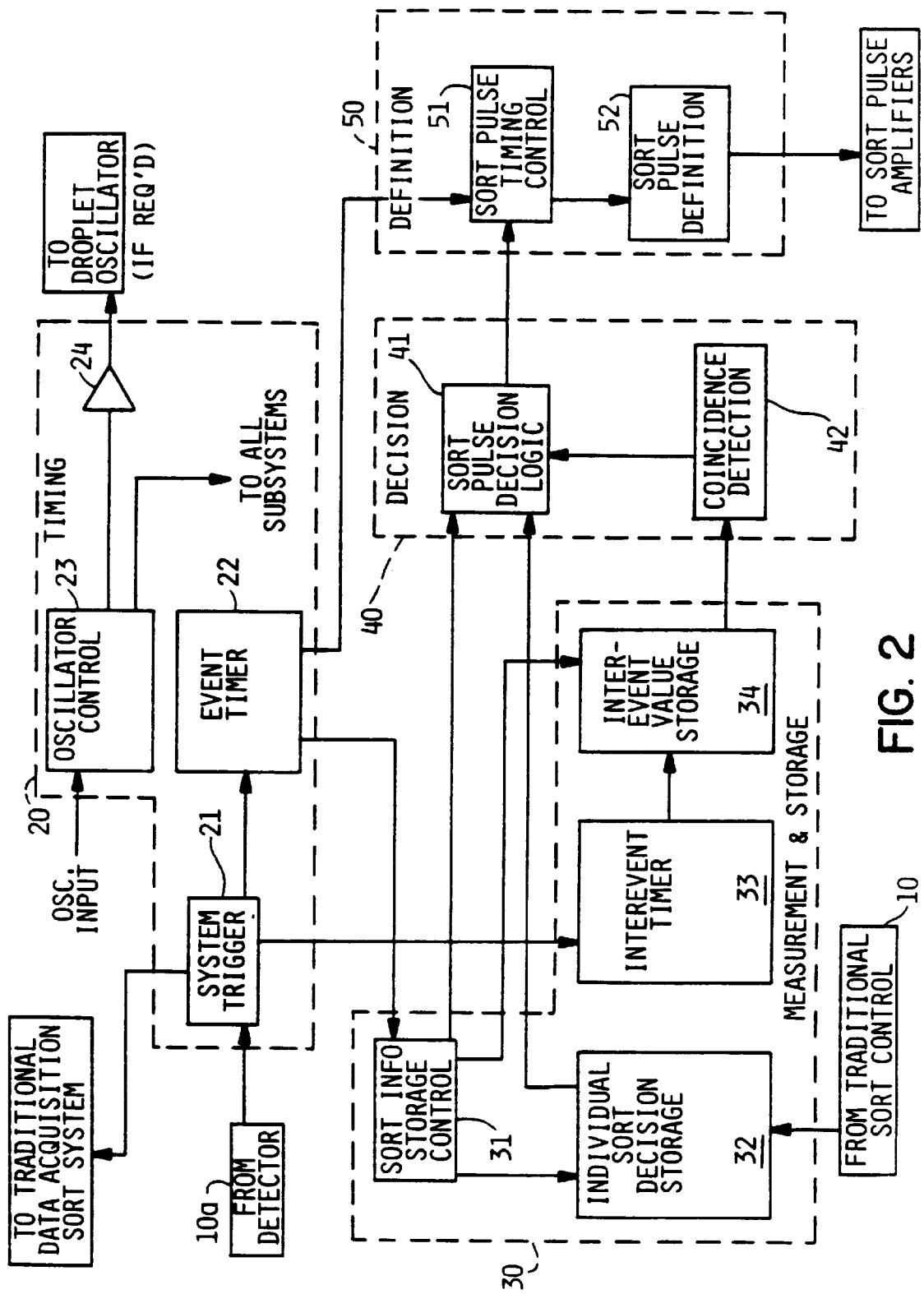
FIG. 2 is a block diagram of a particle sorting system according to an embodiment of the invention.

FIG. 2 illustrates a preferred embodiment of a system constructed in accordance with the present invention. The system receives detection analog input signals from a particle detector 10a, such as a total signal (TOTAL) at the system trigger 21. The TOTAL signal represents a signal generated when any particle passes by a point in the particle detector, i.e. is detected when passing by a laser beam. The incoming TOTAL signal is in the range from noise level to about 10.0 volts, preferably significantly above noise level. The TOTAL signal is received by a system trigger threshold comparator 21b which determines if the received signal has crossed a system trigger threshold reference voltage. The trigger threshold voltage comes from a system trigger threshold source 21a whose voltage level is settable by the user of the system. When the signal received at the comparator has crossed the trigger reference voltage, a TRIGGER signal is generated by the comparator 21b. The TRIGGER signal is applied to an event timer circuit 22, an inter-event timer circuit 33 and a data acquisition system 10b for synchronization of the system 100 with each of the particles detected.

Figure 3A:
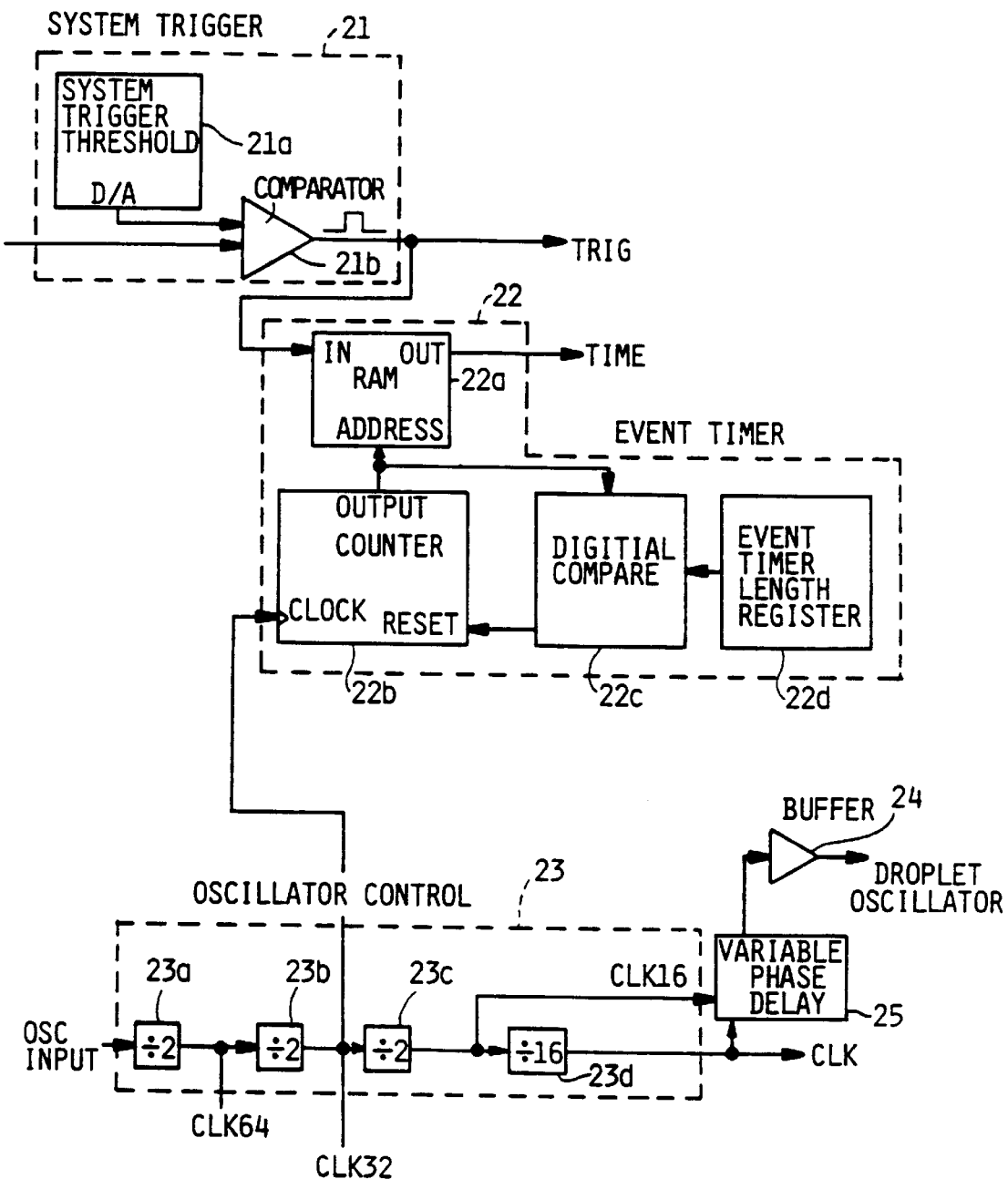
FIG. 3A is a logic diagram of electrical circuitry for timing circuitry according to an embodiment of the invention.

An oscillator control circuit 23 is used as a system clocking source. The oscillator control circuit 23 is adjusted to the frequency of the sorting units (e.g. droplets). In this embodiment of the invention, an input to the oscillator control circuit 23 is user settable and is adjusted to be 128 times the frequency of the droplet stream. The oscillator control circuit 23 establishes clocking rates for different parts of the system by dividing down the input frequency by selected values with division circuits 23a–23d to give required frequencies at the required phases. In FIG. 3a, the different frequencies are shown as CLK 64, CLK 32, CLK 16 and CLK corresponding to the division of the input frequency by 2, 4, 8 and 128, respectively.

In this implementation, system 100 is used for droplet sorting and, therefore, the system provides a droplet oscillator 100. The droplet oscillator 10c is used at the point at which the fluid stream exits an ejection nozzle of the flow cytometer into the air. The droplet oscillator 10c is used during droplet formation such that droplets are formed in a uniform shape and break off from the fluid stream in a stable position. The droplet oscillator 10c comprises a piezoelectric crystal to provide vibratory motion for droplet formation. The droplet oscillator 10c is driven by the oscillator reduced frequency to vibrate the piezoelectric transducer at a resonant frequency of the stream. The resonant frequency used in this implementation is 32 KHZ. In this implementation, the reduced frequency, CLK, to the droplet oscillator 10c is 1/128 of the input frequency. Further, in this implementation of droplet sorting, a variable phase delay circuit 25 is provided to vary the input frequency to the droplet oscillator 10c and is connected to a buffer which leads into a droplet oscillator 10c. The variable phase delay circuit 25 operates to synchronize the sorting of a droplet with the sort pulse charged to the droplet such that a charge is applied to a whole droplet. Since, depending on the flow rate, the distance measured from when the droplet is detected by the system and when a charge is applied to a droplet may not result in a whole droplet being charged, the variable phase circuit delay 25 offsets a droplet by increments of $\frac{1}{16}$ of a droplet to align the charging circuitry with the sorted droplet. Alternative implementations which do not use the system for droplet sorting, for example, destruction of an object by zapping, cellular injection or selective introduction of material to an object do not require a droplet oscillator and the phase delay value is ignored.

Referring to FIG. 2, timing of events of the system is performed with an event timer circuit 22 and an inter event timer circuit 33. An event timer circuit 22 is provided to initiate when a sort decision should be made and to determine when a sort pulse should be applied to a sorting unit or droplet. The event timer circuit 22 measures the length of the stream or the time to be delayed as the particle travels from the sense point to the point at which a charge pulse is applied to a particle. In this implementation, for droplet sorting, the charge should be applied near the point at which droplets break off from the fluid stream. The event time is a relative constant value that is defined by the physical separation of the signal excitation source from the location at which sorting will occur and the velocity at which the object is traveling between the two locations. In this implementation, the event time is approximately 650 microseconds and the velocity at which the cells are travelling is 10 m/sec, and there are from 18–23 droplet lengths from the excitation source to the sorting location.

As shown in FIG. 3A, the event timer circuit 22 comprises a RAM memory 22a, a counter 22b, a comparator 22c and an event timer length register 22d. Timing is accomplished in the event timer circuit 22 with a shift register operation of variable length. In this implementation, the RAM memory 22a comprises a 4k×1 bit RAM with separate input and output pins. This RAM memory 22a is addressed by the value of the counter 22b that is continuously incremented at the CLK 32 frequency described above. When the RAM memory 22a input receives a TRIGGER signal, a value of 1 is stored in the RAM location at the address currently addressed by the counter value. As the counter 22b is continuously incremented, the incremented counter value is inputted to the comparator 22c which compares the counter value with a length value which is stored in the event timer length register 22d. The user settable length value is determined from the physical distance between the excitation point to the point at which the droplet is charged and the flow rate of the stream. This value is in units of $\frac{1}{32}$ of the droplet period. When the comparator 22c determines the counter value is the same as the length value, the counter 22c is reset to zero and is continuously incremented from there in a cyclic manner. A TIME signal is generated by the event timer circuit 22 when the counter 22b has returned to the value during which the trigger signal was stored.

In this embodiment, as shown in FIG. 2, the system provides an inter-event timing circuit 33 for measuring the time between system triggers of successive events or inter-event time. This inter-event time is used to determine when events are coincident. In this implementation, coincident events are defined as two or more events being close enough in proximity to each other in the fluid stream to be in the same sorting unit, e.g. the same droplet in droplet sorting.

Figure 3B:
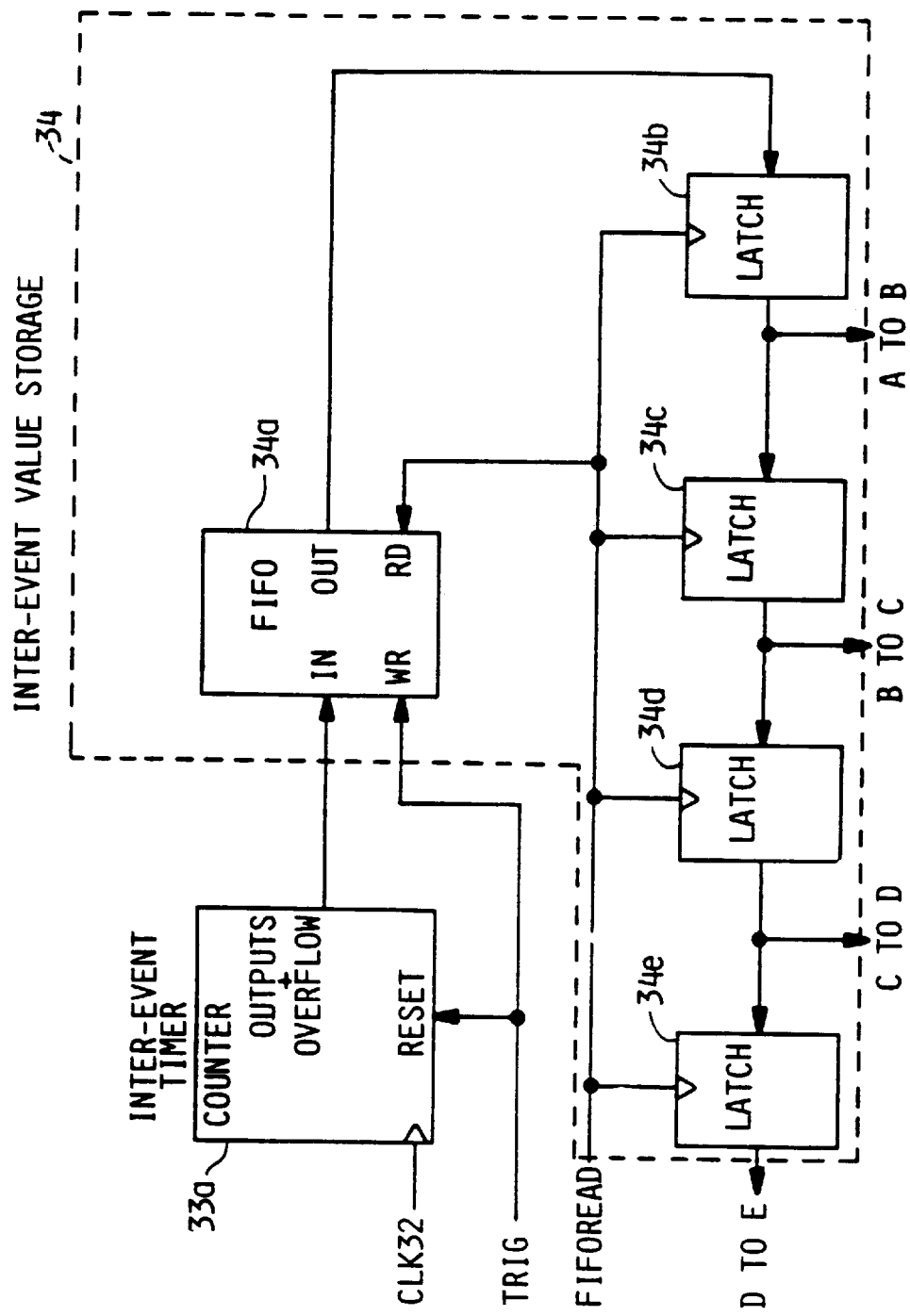
FIG. 3B is a logic diagram of electrical circuitry for 1S measurement and storage circuitry according to an embodiment of the invention.

Referring to FIG. 3B, this inter-event timing is accomplished by a counter 33a that is continuously incremented by the same frequency as the event timer circuit 22, i.e. 32 times the droplet frequency by receiving a CLK32 signal. The counter 33a is responsive to the TRIGGER signal such that each time a TRIGGER signal is received the value of the counter 33a is read into an inter-event FIFO memory 34a. After reading the inter-event time the counter 33a is reset to zero to begin counting the time to the next event. In this implementation, the value of the counter is eight bits and the counter values will range from 0 to 255. In the case that events are farther apart than the counter's maximum value, i.e. 255, an overflow of the counter 33a is latched and infinite separation is assumed.

In system 100, as a particle or cell passes a detector, a data acquisition system 10b determines an individual sort decision based on the parameters detected for the characteristics of the detected particle. The individual sort decision can be a decision to sort the particle, i.e., sort right or sort left, or not to sort the particle. A signal line for each of the sort left or sort right decisions is fed from the data acquisition system 10b to an individual sort decision storage circuit 32 for storing individual sort decisions. When the data acquisition system 10b makes a sort right or sort left decision, a one value is sent to the individual sort storage circuit 32 on the appropriate line. If the data acquisition system 10b makes a no sort decision, a zero value is sent on both the sort left and sort right lines. The individual sort decision storage circuit 32 comprises a sort FIFO memory 32a and a predetermined number of latches 32b–32k corresponding to the number of events or cells which will be available for making a sort decision, as described below, The sort FIFO memory 32a of the individual sort decision circuit 32 is controlled by a sort information storage control circuit 31. The sort information storage control circuit 31 is adapted to control the reading of the sort FIFO memory 32a such that information on a current detected cell as well as information on cells which were detected before and after the current cell can be latched in appropriate latches 32b–32k, so that the data in the latches at a particular instant in time is available for making a sort decision.

Figure 4:
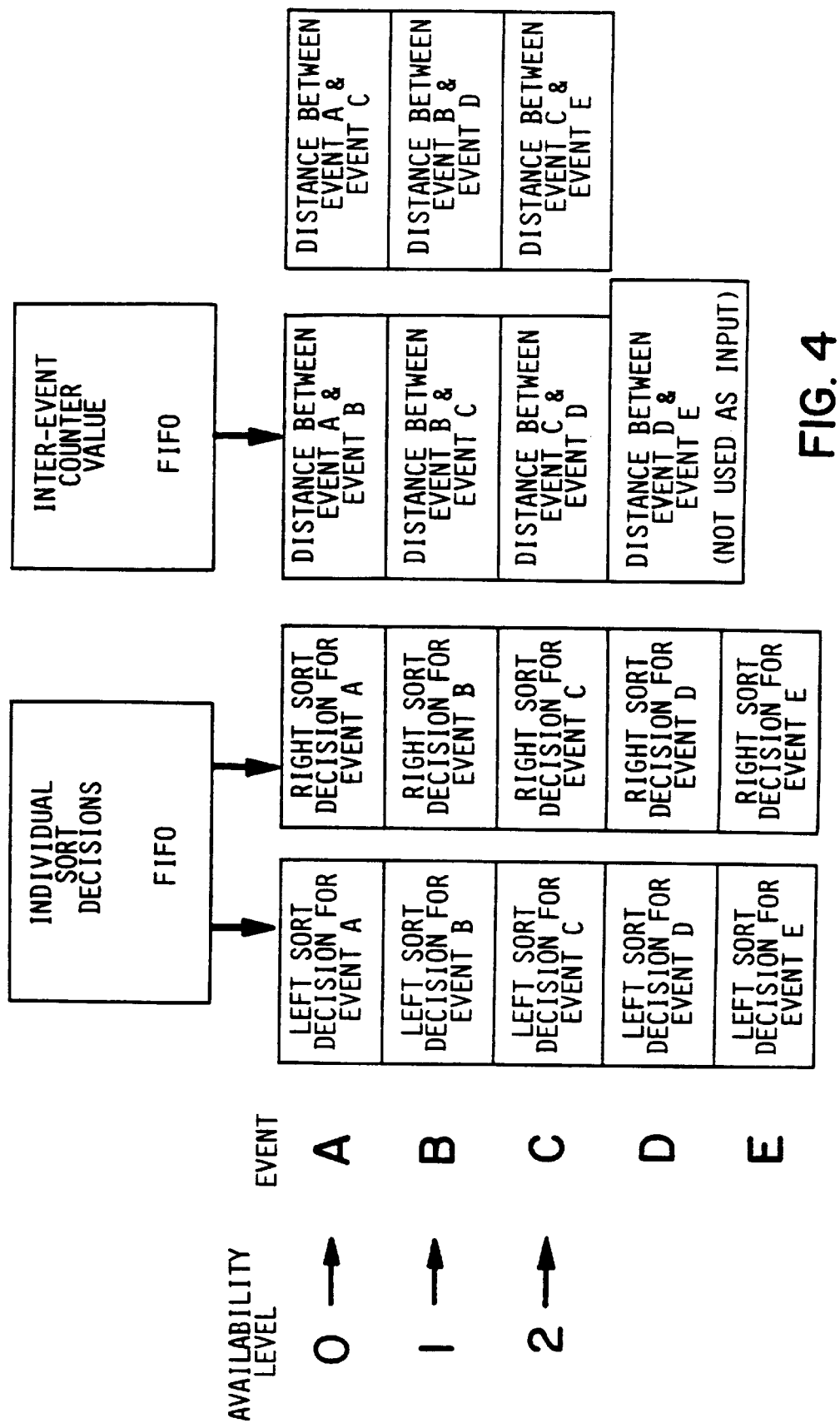
FIG. 4 is an illustration of data available for a look-up table for a sort pulse decision.

The sort information storage control circuit 31 is responsive to an AVAILABILITY LEVEL variable which indicates the number of events before and after the currently detected cell that may be used by the sort decision logic of the system when making a sort decision. As illustrated in FIG. 4, in this implementation, the AVAILABILITY LEVEL for a sort decision can have the values of 0, 1 or 2. In the initial operation of the sort information control circuit 31 the AVAILABILITY LEVEL is set to "−1", indicating no cells are available for a sort decision. When the first cell or current event is detected by the system, the AVAILABILITY LEVEL will change to "0" as described below, indicating only the current event or cell can be used in making a decision at that instant, since no prior cells were detected. The sort decision for the cell detected by the system is considered to be event A, as shown in the first row of FIG. 4, and may have values of left sort decision or right sort decision. The sort FIFO memory 32a is updated by the sort information storage control circuit 31 in response to the CLK32 signal for continuously determining if information on an event has been stored in the sort FIFO memory 32a. In operation of the system the sort FIFO memory 32a is checked at a rate of 32 times per droplet, and if the sort FIFO memory 32a is empty an empty signal will be sent to the sort information storage control unit. A strobe signal is sent to the sort FIFO memory 32a to indicate an event has arrived at the sort FIFO memory 32a.

A FIFO READ signal is generated whenever an event has been stored in the'sort FIFO memory 32a, the sort FIFO memory 32a is not empty, and the availability level is less than AVAILABILITY LEVEL "2". AVAILABILITY LEVEL "2" is the maximum availability level for this implementation. The combination of the NOR gate 31a and AND gate 31b are used to generate the FIFO READ signal. The NOR gate 31a operates on the EMPTY signal and the AVAILABILITY LEVEL. When neither an EMPTY signal or an AVAILABILITY LEVEL of "2" is received, a FIFO READ SIGNAL is generated to the AND gate 31b. In response to the AND circuit receiving a CLK 32, the FIFO READ signal is applied to the inter-event FIFO memory 34a and the sort FIFO memory 32a. If the state of the sort FIFO memory 32a, where the FIFO is not empty and the AVAILABILITY LEVEL is less than 2, indicates that information is available in the sort FIFO memory 32a, which is available to be read into the chain of latches 32b–32k, then this information is made available for sorting decisions.

The FIFO READ signal is also applied to counter 31c for updating the AVAILABILITY LEVEL. Before a FIFO READ signal is applied to the availability level counter, nothing is in the queue and both QA and QB of the counter 31c are low or zero. In response to the first FIFO READ signal, QA is set to 1, QB remains at 0 and the output of AND circuit is 0, i.e. AVAILABILITY LEVEL 0. In response to a second FIFO READ signal being applied to the availability level counter 31c, QA is set to 0, QB is set to 1, the output of the AND circuit is 0 and the output of QB is one, indicating AVAILABILITY LEVEL 1. In response to another FIFO READ being applied to the counter 31c, both QB and QA are set to 1 such that the AVAILABILITY LEVEL is set to 2.

When the first individual sort decision was received from the data acquisition system 10b, as described above, a FIFO READ signal is generated, since the sort FIFO memory 32a is no longer empty and the AVAILABILITY LEVEL is less than 2. The sort FIFO memory 32a is responsive to the FIFO READ signal and the first event stored in the sort FIFO memory is moved into latches 32b, 32g. Therefore, a LEFT A or RIGHT A decision is available in latches 32b, 32g for making a sort decision.

Once a subsequent individual sort decision arrives at the sort FIFO memory 32a and is stored in the sort FIFO memory 32a, a FIFO READ signal is again produced, since the sort FIFO memory 32a is not empty and AVAILABILITY LEVEL is less than 2, and a signal is applied to counter 31c. In response to the FIFO READ signal, data in the sort FIFO memory is read to latches 32b, 32g and the data originally in latches 32b, 32g is moved to latches 32c, 32h, respectively.

As illustrated in FIG. 4, the data which was previously stored in event A is moved to event B when the AVAILABILITY LEVEL is set to 1. In this case, AVAILABILITY LEVEL of 0 would indicated a subsequent event was received and stored in event A and AVAILABILITY LEVEL 1 indicates that the event data which was previously received and stored in event A is now stored in event B. Therefore, for AVAILABILITY LEVEL 1 when making a sort decision. The sort decision has available the data in event B, the current event to be sorted, as well as the data in event A, data received after the current event but before a logic decision is made.

In the event another individual sort decision is received, at the sort FIFO memory 32a, the counter 31c generates a TWO value at QB to indicate an AVAILABILITY LEVEL of two. A FIFO READ signal is generated to move the latched data from 32b, 32g to 32c, 32h and previously stored 32c, 32h to 32d, 32i, respectively. At this time, the maximum availability level has been reached for this implementation and the TWO value from the counter 31c is applied to the NOR gate 31a to disable generation of the FIFO READ signal. As shown in FIG. 3, when the AVAILABILITY LEVEL is set to "2", information is available for events A, B and C. The value of the counter will remain at TWO until the time at which a logic sort decision is made. When a logic sort decision is to be made, a TIME signal from the event timer is applied to the counter 31c. In response to the TIME signal, the counter 31c decrements the AVAILABILITY LEVEL by one, after the logic sort decision has been made.

As shown in FIG. 4, an event which arrives after data has been previously stored in events A, B and C will be moved into Event A and move previously stored data in Event A to Event B, Event B to Event C and Event C to Event D by moving data from latch 32b to 32c, 32c to 32d, 32d to 32e and 32e to 32f and data from latch 32g to 32h, 32h to 32i, 32i to 32j and 32j to 32k. In this implementation, event E is the last Event for storing data corresponding to the maximum availability for a sorting decision of two events prior to the event to be stored and two events after the event to be sorted. Alternative embodiments can include a different number of latches to correspond to the use of more or less events before and after the event to be sorted when making a sorting decision.

Referring to FIG. 2, coincident detection circuit 42 receives the values of the inter-event value storage circuit 34 which corresponds to the inter-event times and an over flow bit value storage circuit for determining if two or more events, i.e. system triggers, are within a user specified time period. The time period is established by the user and is set in the coincident value register 42a with 8 bits so that the value ranges from 0 to 255. The coincident value is in the same units as the inter-event counter values. Digital comparators 42e–42j are used to determine if the coincident value register 42a is greater than the values received from the inter-event storage circuit 34, thereby indicating the events are coincident. The coincident detection circuit 42 includes sum circuits 42b–42d which are used to determine if more than two events are coincident if the distance between two events, A to C, is less than the coincident value. The sum circuits 42b–42d sum the lengths between two events, i.e., A to B and B to C, and the value is compared in respective comparator 42e, 42g and 42i. If the sum of event A to B and B to C is less than the coincident value, the events A, B and C are coincident.

The inter-event FIFO memory 34a is read in response to the FIFO READ signal, described above. The FIFO READ signal is used to read information stored in the inter-event FIFO memory into a chain of latches 34b–34e so that the inter-event timing information for each object is available when making sort pulse decisions. On receiving the FIFO READ signal at the inter-event FIFO memory, the first inter-event corresponding to A to B is read into latch 34b. As FIFO READ signals are generated, data is moved from latch 34b to 34c, 34c to 34d and 34d to 34e corresponding to inter-events corresponding to A to B, B to C, C to D and D to E.

The sort pulse decision logic circuit 41 uses the individual sort decisions and inter-event times of nearby events to generate a sort pulse decision appropriate for the current event, based on the strategy chosen. This strategy is user definable and may be altered to allow for any combination of purity vs. yield to be implemented.

Figure 3C:
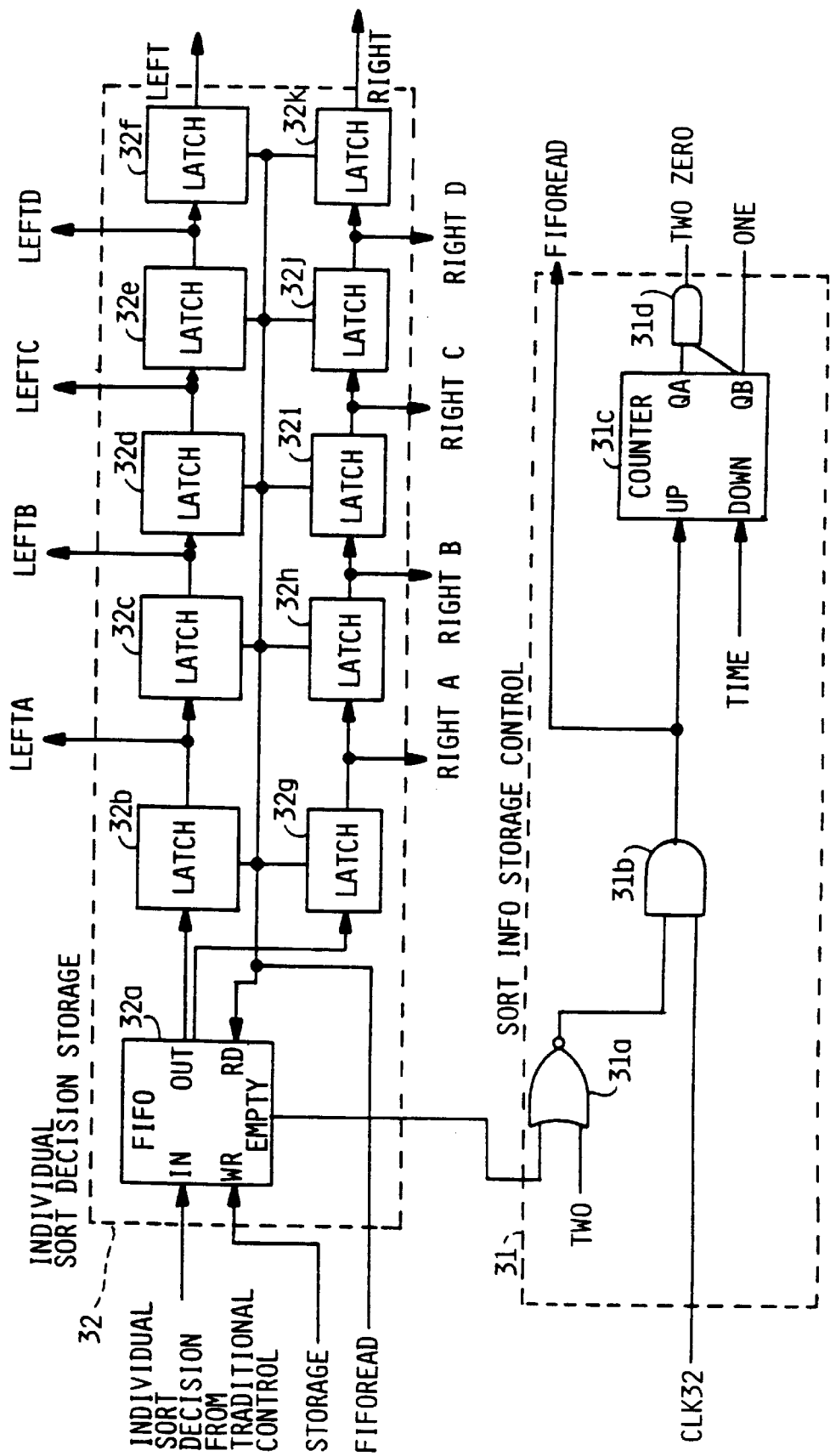
FIG. 3C is a logic diagram of electrical circuitry for sort decision circuitry according to an embodiment of the invention.

As illustrated in FIG. 3C, a sort pulse decision in this implementation is made based on 18 conditions and is directed by a user defined strategy (e.g from mathematical modeling). The 18 conditions are used as inputs to a sort pulse decision logic RAM look-up table 41 which is loaded with a transfer function embodying the user defined strategy.

The inputs to this look-up RAM table 41 are information pertaining to up to five available events (i.e. events A through E). Ten of these inputs are the left and right individual sort decisions of each of the five possible events (A through E) from latches 32b–32k. Three more inputs indicate whether, or not, there is coincidence (as defined above) between neighboring events (i.e. between events A&B, B&C, C&D) from digital comparators 42e, 42g and 42i. There are also three inputs that indicate coincidence between events that are separated by two (i.e. between events A&C, B&D, C&E) from comparators 42f, 42h and 42j.

In this embodiment coincidence is defined by setting a register with the maximum time spacing at which two events will be considered coincident. This value is in units of 1/32 of the droplet period and is used as the compare value with the inter-event counter values stored at each system trigger.

Two more inputs to the RAM look-up table 41 are used to indicate the number of available future events. as described above (AVAILABILITY LEVEL). The availability level also indicates which information is that of the current event (i.e. for AVAILABILITY LEVEL 0, event A is the current event; for AVAILABILITY LEVEL 1, event B is the current event; for AVAILABILITY LEVEL 2, event C is the current event). The transfer function of the look-up table (i.e. strategy) may be developed using boolean logic on mode control variables. Some examples of boolean variables that may be used are:

1: SORT LEFT ENABLE Enables the sort left output.
2: SORT RIGHT ENABLE Enables the sort right output.
3: LEFT ANTICOINCIDENCE WITH RIGHT ENABLE Generates left sort outputs such that they will not be coincident with right sort events.
4: RIGHT ANTICOINCIDENCE WITH LEFT ENABLE Generates right sort outputs such that they will not be coincident with left sort events.
5: LEFT ANTICOINCIDENCE WITH NEUTRAL ENABLE Generates left sort outputs such that they will not be coincident with neutral (neither left nor right sort) events.
6: RIGHT ANTICOINCIDENCE WITH NEUTRAL ENABLE Generates right sort outputs such that they will not be coincident with neutral (neither left nor right sort) events.
7: LEFT—CHECK NEAR NEIGHBOR ENABLE Generates left sort outputs taking into consideration the coincidence of events that are immediately preceding or following the event in question.
8: RIGHT—CHECK NEAR NEIGHBOR ENABLE Generates right sort outputs taking into consideration the coincidence of events that are immediately preceding or following the event in question.
9: LEFT—CHECK FAR NEIGHBOR ENABLE Generates left sort outputs taking into consideration the coincidence of events that are two events preceding and two events following the event in question.
10: RIGHT—CHECK FAR NEIGHBOR ENABLE Generates right sort outputs taking into consideration the coincidence of events that are two events preceding and two events following the event in question.
11: LEFT SORT DOMINANCE ENABLE When an event has an individual sort decision that is in overlapping regions (both sort left and sort right) it will be treated as a sort left individual sort decision.
12: RIGHT SORT DOMINANCE ENABLE When an event has individual sort decision that is in overlapping regions (both sort left and sort right) it will be treated as a sort right individual sort decision.

In alternative implementations, other variables may be defined and algorithms to control them in order to generate a look-up table corresponding to a wide range of experiment environments.

Other non-boolean variables can be incorporated into the strategy to define a purity/yield ratio giving a minimum purity requirement.

In this Case, the user defines a maximum acceptable purity level (given as percent here for example) and that purity is compared as a threshold to the sort unit under consideration. Examples of rules used in the sort pulse decision logic for sorting in a single direction are as follows:

1: IF TWO CELL ARE COINCIDENT WITHIN A SINGLE SORTING UNIT
 if only one is desired then 50% purity results.
 if both are desired then 100% purity results.
2: IF THREE CELLS ARE COINCIDENT WITHIN A SINGLE SORTING UNIT
 if only one is desired then 33% purity results.
 if two are desired then 67% purity results.
 if all are desired then 100% results.
3: IF FOUR CELLS ARE COINCIDENT WITH A SINGLE SORTING UNIT
 if only one is desired then 25% purity results.
 if two are desired then 50% purity results.
 if three are desired then 75% purity results.
 if all are desired then 100% purity results.
4: IF FIVE CELLS ARE COINCIDENT WITHIN A SINGLE SORTING UNIT
 if only one is desired then 20% purity results.
 if two are desired then 40% purity results.
 if three are desired then 60% purity results.
 if four are desired then 80% purity results.
 if all are desired then 100% purity results.

In this strategy, we assume that the arrival statistics of each cell subpopulation (e.g. desired, undesired) are independent of each other. Prior knowledge of the overall percentage of each cell type is then used to develop an overall model of the probability of each cell type for each of the above sorting unit rules to determine the yield of each sorted subpopulation.

Each of the above conditions may be separately defined as a sort or no sort condition. By incorporating these rules with a knowledge of the statistical probability of each condition occurring (i.e. a mathematical model), an optimized strategy can be developed.

Other examples of purity driven strategies consider other conditions and permutations such as the conflicting purities of "sort right" and "sort left" cells (i.e. two direction sorting) in making a sort decision.

In a preferred embodiment, the look-up table is implementated in RAM 41 to allow a flexible definition of the sort pulse decision process. The look-up table 41 may be quickly altered by the user to define special modes of operation by loading it with new transfer data which may have been generated earlier. The output of the look-up table is a sort left or sort right logic decision.

Figure 3D:
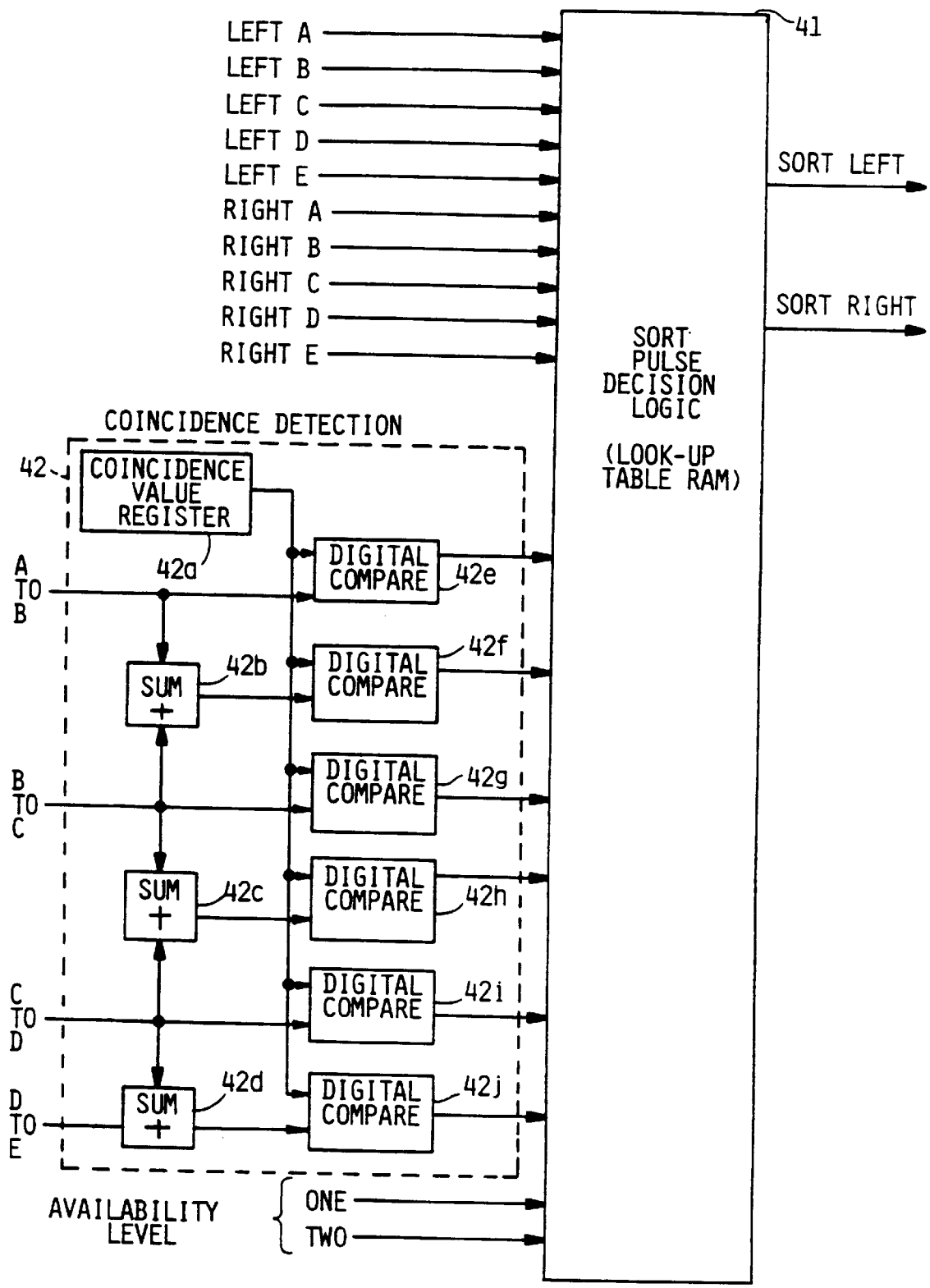
FIG. 3D is a logic diagram of electrical circuitry for sort pulse definition circuitry according to an embodiment of the invention.
Figure 3E:
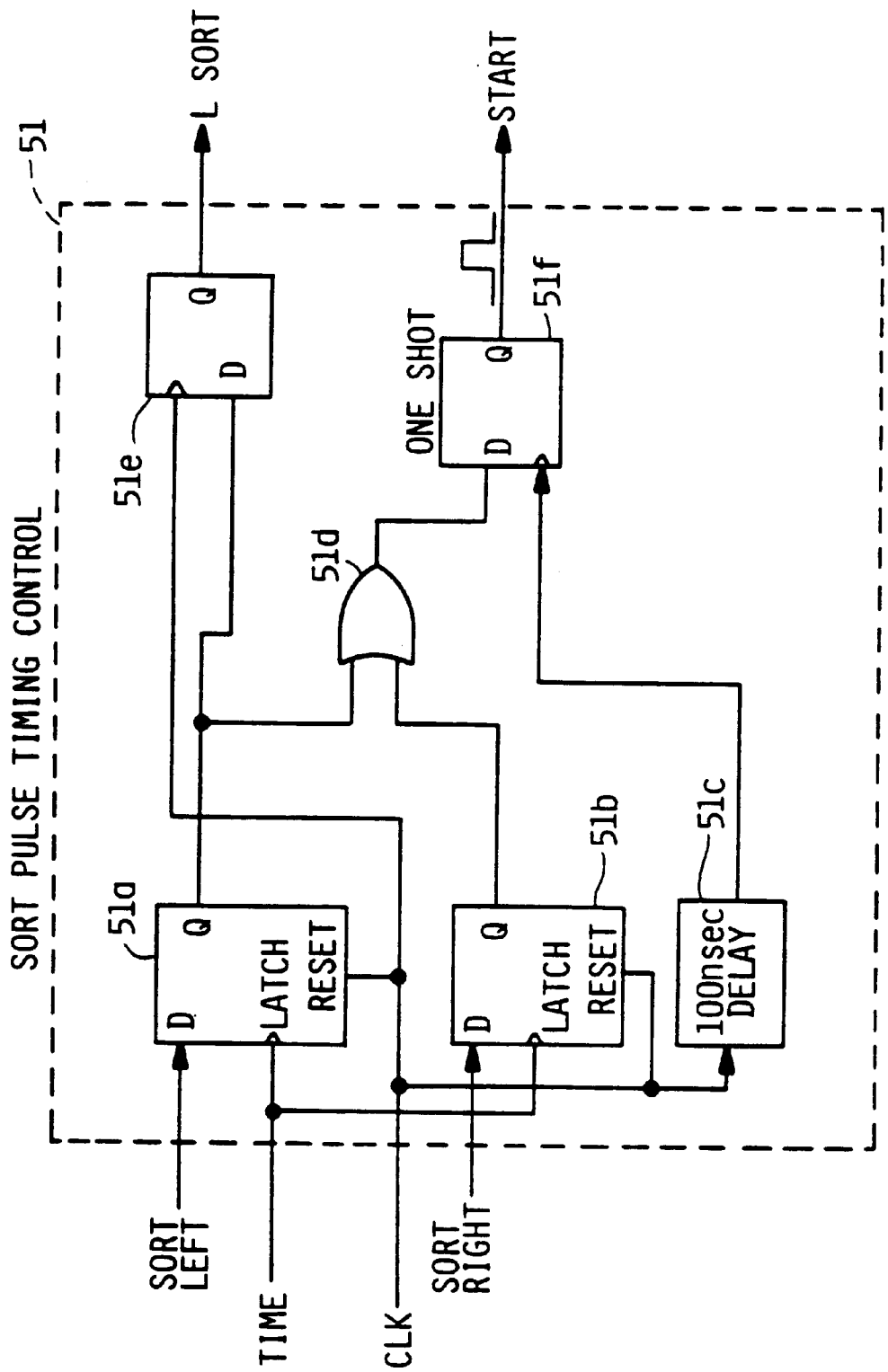
Figure 3F:
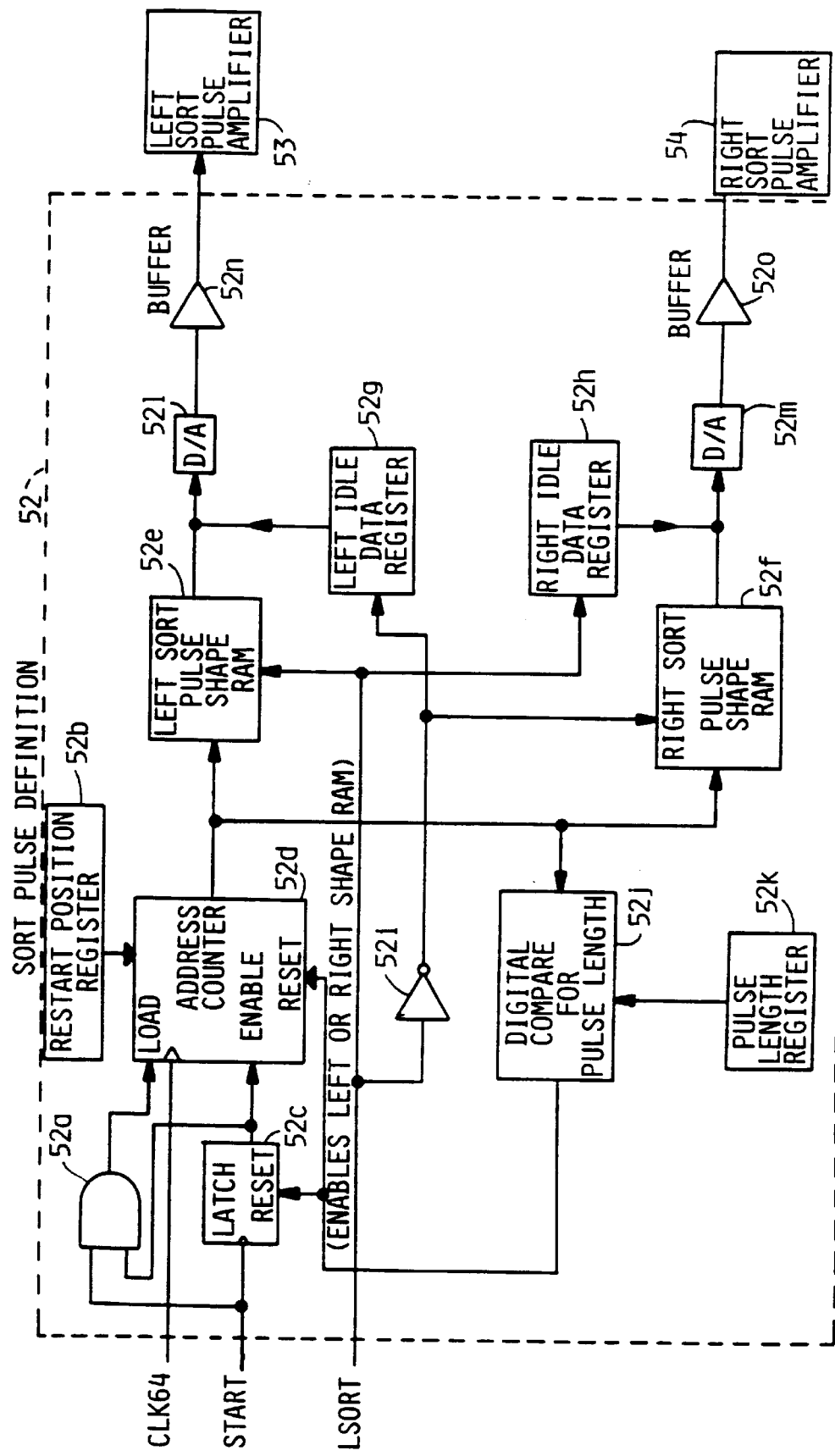

Referring to FIGS. 2 and 3D, there is shown a sort pulse timing control circuit 51 for starting the sort pulse in response to the TIME signal from the event timer circuit 22 indicating the time for the droplet to travel from the detector to droplet break-off has lapsed. The sort pulse timing control circuit 51 only applies a sort pulse to droplets which are to be sorted. A sort left or sort right decision from the sort pulse decision logic circuit 41 is received at the D input of latch 51a and latch 51b, respectively. The latches are synchronized with a CLK signal in order to synchronize the pulse with a droplet. The sort pulse timing control circuit 51 operates on the condition that the droplet must be physically sorted either left or right and can not have both a sort left and sort right condition concurrently. In this implementation, the sort pulse timing control circuit 51 determines a condition as either sort left or not sort left. If a left sort is received at latch 51a, the Q output of latch will be high and will be fed to latch 51e as the D input. The latch 51e will output a LEFT SORT signal. Also, the Q output of latch 51a is applied to an OR gate 51d to be combined with the Q output of latch 51b. Since a LEFT SORT decision was received at latch 51a, a high signal is generated as input to ONE-shot latch 51f which generates a START pulse. The ONE-shot latch operates on a CLK signal which is delayed by 100 nsec with a digital delay circuit 51c to account for the time needed for the latches to propagate. If a right sort decision, is received at latch 51a, a START signal will be generated by ONE-shot latch 51f, but a left sort decision will not be generated by the sort pulse timing control circuit 51. Therefore, indicating a not left condition.

The left sort signal and the START signal are applied to a sort pulse definition circuit 52 to define the sort pulse for each of the two directions. The pulse is defined by a series of amplitude values (8-bit) stored in a left sort pulse shape RAM 52e and right sort pulse shape RAM 52f. The sort pulse shape definition data may be defined using many different techniques including, but not limited to, mathematical waveform description, real waveform capture and digitization or some combination thereof. The resulting data is then loaded into the sort pulse definition circuit's left sort pulse shape RAM 52e and right sort pulse shape RAM 52f. When a START pulse signal is received by the sort pulse definition circuit 52, the values in either the left sort pulse shape RAM 52e or the right sort pulse shape RAM 52f, in response to the presence or absence of a left sort condition, are sequentially output to a digital-to-analog converter (DAC) 52l for the left sort pulse shape RAM 52e, or 52m for the right sort pulse shape RAM 52f at a frequency of 64 times the oscillator frequency. The DAC's 52l or 52m output is used to define the shape of the sort pulse. In this implementation, the output voltage is between 0–5 volts. This output is amplified to a higher voltage value if required by external amplifiers 53 or 54, i.e. up to 10 times the voltage from the DAC.

The values in the left sort pulse RAM 52e and right sort pulse RAM 52f are addressed for the DAC 52l or 52m by an address counter 52d which is started when a start pulse is received by latch 52c. This address counter 52d is incremented at a frequency of 64 times the droplet oscillator frequency. The address counter 52d continues until a user determined pulse length set by the pulse length register 52k has been reached. A pulse length register 52k stores predetermined values for the length of the pulse to determine the number of droplets which the pulse will be applied to, for example, the length value would be 64 for a 1 droplet length pulse or 128 for a 2 droplet length pulse. At this time, the address counter 52d is reset to zero, the sort pulse is stopped and the sort pulse definition circuit 52 is ready to receive another START sort pulse signal.

If a START sort pulse signal is received while a sort pulse is already in progress, the address counter 52d that addresses the RAM data will be set to a user defined value and the sort pulse continues from there. This value in restart position register 52b, defines the position in the pulse definition where an overlapping sort pulse should begin to avoid pulse distortions caused by pulse rise profiles being executed mid-pulse. This allows long pulses to overlap without causing a distortion of the pulse shape. The pulse length may continue for multiple pulses, each pulse overlapping the one before it. A left idle data register 12g and a right idle data register 12h are provided to define the output value of the sort pulse while that sort direction is disabled (i.e. a sort pulse in another direction is in progress).

System 100 maintains two possible sort directions and allows each sort direction to have a separately definable sort pulse shape. Both of these sort pulses have a separate DAC, 52l and 52m, and output by external buffers 52n and 53o which may be combined into a composite sort pulse by amplifier circuits 53 and 54. Since only one address counter is used in this implementation, pulses are generated for only one output at a time while the other is disabled. The RAM address counter 52d enables the left sort RAM if a left sort signal is received and enables the right sort RAM if a left sort signal is not required. A user defined value is output when a sort direction is disabled. It is assumed that the anti-coincidence circuitry above is adjusted such that overlapping pulses of opposite direction will not occur.

In a preferred embodiment of the present invention, the system 100 provides a Q-bus extension to a PDP-11/73 computer system which is used to implement user interface and system setup functions. In alternative implementations other computer systems may be used to perform these functions, i.e. an IBM PC/AT compatible personal computer (PC). The PC is a more widely available platform and would thus allow implementation of this system over a wider range of applications. The PC platform can also be used for mathematically modeling our systems and sort control strategy planning.

Figure 5:
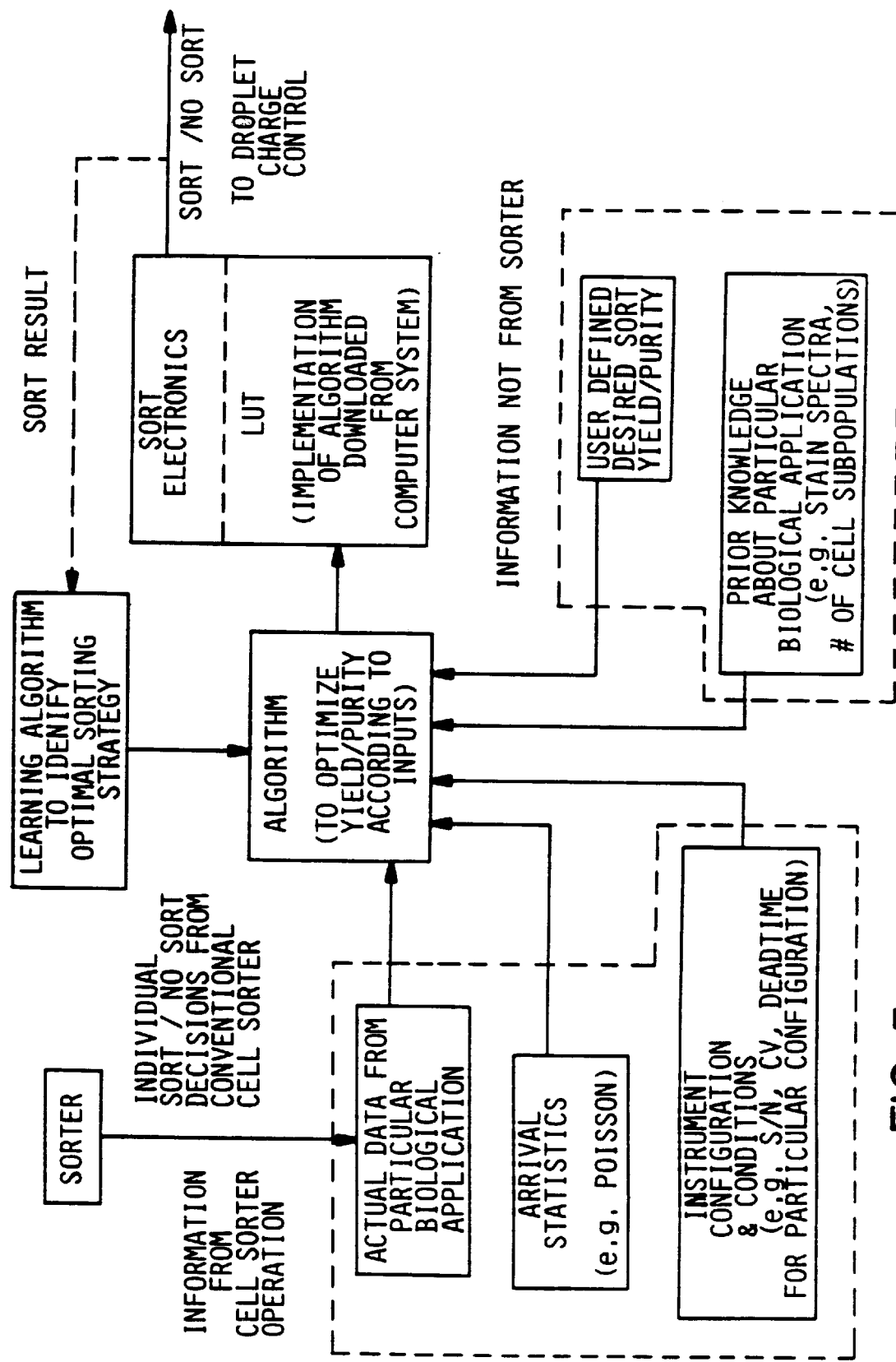
FIG. 5 is a schematic block diagram of software modules according to an embodiment of the invention.

As illustrated in FIG. 5, in this implementation a software algorithm is used to identify the optimal sorting strategy. The algorithm uses information from the cell sorter operation which include individual sort or no sort decision from the traditional sort control 10, i.e. event A, B, C, D, E and interevent A to B, B to C, C to D, D to E, which are the same inputs stored in the RAM 41 as the information from the detection signals generated in response to the respective particles passing a selected point of the flow cytometer. Further, the alogrithm uses arrival statistics of the particles, i.e. poisson, and conditions of the instrument, i.e. signal/noise ratio, coefficient of variation of the signals or deadtime between particles, to enable particles to be separated on determination of a yield/purity ratio that is specific to the implemented hardware. Specifically, the coefficient of variation of signals is used to offset variations of the instrument caused by the environment of the instrument, i.e. temperature or humidity. The algorithm may also use information not from system 100 such as user defined logic conditions for yield/purity ratios and prior knowledge about a particular experiment. For example, prior knowledge may include stain spectra and a value of the number of cell subpopulations present in the sample. The algorithm optimizes the yield/purity ratio according to the information received. The algorithm provides the logic for the RAM look-up table (LUT) to determine a sort decision and controls the hardware circuitry of system 100. After a decision has been made to sort or not to sort the droplet, the sort result is passed to a learning algorithm to identify if the sort decision resulted in the correct yield/purity ratio and to modify the algorithm to optimize the desired yield/purity ratio.

In an alternative embodiment, each sort direction may have its own separate address counter and thus allow overlapping sort pulses of many sort directions to be implemented to allow any number of possible pulse shapes to be used as a dynamic function of current conditions. An example of this feature may be to use different charge shapes (droplet sorting) if the object was in the neck area of the droplet at breakoff. Another use would be to alter the pulse shape (including duration ) and/or amplitude depending on number and/or type of objects within a given sorting unit.

Another alternative embodiment of the invention, monitors events which are characterized as "missed events". A "missed event" is defined as an event which arrives during the time intervals that the traditional sort control system is analyzing a previous event and the "friend" or "foe" status of that event is, therefore, unknown. "Missed-event" information may be used by the sort pulse decision logic since there are applications (e.g. sorting of rare cells) where the "friend" or "foe" status of the "missed-event" may or may not be relevant for subsequent processing of the sorted cells.

Further, alternative embodiments may use system 100 for purposes other than sorting. The sorting function may be replaced by any function desired to be performed on an object in flow. Examples of this may include, but are not limited to, selective chemical injection of objects (e.g cellular injection), selective destruction of objects (e.g. zapping), or selective introduction of catalytic force or material to an object. In a further alternative embodiment the system may be used with systems other than flow systems. Any system in which objects are in closer proximity than the function's effector can resolve could use system 100.

In an alternative embodiment, the traditional sort control which provides a binary sort/no sort decision may be replaced with a non-binary decision. In this implementation the logic of sorting system would be coordinated to determine a sorting decision using the non-binary decision values.

Another alternative embodiment of the invention monitors an event's relative position within the sorting unit. This may be used as an alternative means of detecting coincidence of multiple events. This relative position may also have a probability "confidence factor" associated with it, for example to allow for the small instabilities in droplet formation.

It will also be appreciated that various modifications, alternate construction and equivalents may be employed without departing from the spirit and scope of the invention and that, therefore, the above description and illustration should not be construed as limiting the scope of the invention, which is defined by the appended claims.

We claim:

1. A method for sorting particles comprising:

receiving detection signals representing selected parameters of moving particles from a sensor;

generating respective trigger signals and a respective individual sort decision in response to the detection signals received from said sensor;

detecting an overlap condition of successive respective trigger signals in response to time separation between trigger signals of less than selected intervals and producing respective overlap detecting signals in response to the overlap condition;

determining a logic condition in response to a selected combination of the respective individual sort decisions and the overlap detecting signals; and applying a sort pulse to the moving particles when a selected yield/purity ratio which includes intermediate values between maximum yield and maximum purity correspond to a selected logic condition.

2. A method for sorting particles as in claim 1 further comprising:

defining the value of the sort pulse based on the logic condition.

3. A method for sorting particles as in claim 1, wherein said steps for sorting particles are performed with a control system comprising:

timing circuitry receiving said detection signals generated by said sensor and generating a trigger signal after a predetermined time interval for each of [the input] said detection signals generated by said sensor;

inter-event counting circuitry for receiving the trigger signals generated by said timing circuitry and incrementing an inter-event counter in response to said detection signals generated by said sensor received within said predetermined time interval;

inter-event storage circuitry for storing values of said inter-event counter;

sort decision storage circuitry for storing sort decision values for respective characteristics of said particles;

sort decision control circuitry receiving the trigger signal generated by said timing circuitry and thereby updating an availability level variable in response to the trigger signal generated by said timing circuitry;

said sort decision control circuitry generating a read storage signal for respectively reading sort decision values from said sort decision storage circuitry and values of said inter-event counter from said inter-event storage circuitry in response to the trigger signal generated by said timing circuitry;

comparing circuitry coupled to said inter-event storage circuitry, for comparing said respective values of said inter-event counter with a predetermined value to thereby generate compared values when said respective values of said inter-event counter are less than said predetermined value; and logic decision circuitry receiving said respective sort decision values from said sort decision circuitry, said availability level variable updated by said sort decision control circuitry, and said compared values generated by said comparing circuitry, and generating said sort pulse.

4. A method for sorting particles as in claim 1, wherein said steps for sorting the particles are performed with a control system comprising:

a timing circuit which receives the detection signals from said sensor and generates a respective trigger signal;

an overlap detection circuit responsive to successive trigger signals generated by said timing circuit, to generate respective overlap detecting signals in response to time separation of less than selected intervals;

a sort logic circuit responsive to the trigger signals generated by said timing circuit, the detection signals and the overlap detecting signals generated by said overlap detection circuit, to generate respective sort pulses to be applied to the respective particles.

5. A method for sorting particles comprising:

generating input signals for particles from a sensor;

receiving said input signals generated by said sensor using timing circuitry and generating a trigger signal with said timing circuitry after a predetermined time interval for each of the input signals generated by said sensor;

receiving the trigger signals generated by said timing circuitry with inter-event counting circuitry and incrementing an inter-event counter in response to said input signals received within said predetermined time interval;

storing values of said inter-event counter in said inter-event storage circuitry;

storing sort decision values for respective characteristics of the particles;

receiving the trigger signal generated by said timing circuitry with sort decision control circuitry and updating an availability level variable in said sort decision control circuitry in response to the trigger signal generated by said timing circuitry;

generating a read storage signal with said sort decision control circuitry for respectively reading sort decision values from said sort decision storage circuitry and values of said inter-event counter from said inter-event storage circuitry in response to the trigger signal generated by said timing circuitry;

comparing said respective values of said inter-event counter with a predetermined value to generate compared values when said respective values of said inter-event counter are less than said predetermined value; and receiving said respective sort decision values from said sort decision circuitry, said availability level variable updated by said sort decision control circuitry, and said compared values generated by said comparing circuitry, with logic decision circuitry, and generating with said logic decision circuitry a sort pulse signal for the particles in response to the trigger signal generated by said timing circuitry whenever a selected yield/purity ratio which includes intermediate values between maximum yield and maximum purity occurs.

6. A method for sorting particles as comprising:

generating detection signals pertaining to selected parameters for respective particles in response to the respective particles passing a selected point;

receiving the detection signals with a timing circuit, and generating a respective trigger signal;

generating respective overlap signals in response to time separation of less than selected intervals, with an overlap detection circuit responsive to successive trigger signals generated by said timing circuit;

generating respective sort logic signals to be applied to the respective particles whenever a selected yield/purity ratio which includes intermediate values between maximum yield and maximum purity correspond to a selected logic condition, said sort logic signals being generated by a sort logic circuit responsive to the trigger signals generated by said timing circuit, the detection signals and the overlap signals.

* * * * *